United States Patent
Brewer

[11] Patent Number: 5,950,644
[45] Date of Patent: Sep. 14, 1999

[54] DENTURE CLEANSER

[76] Inventor: Edward N. Brewer, 403 Mills Ave., Dumas, Tex. 79029-4114

[21] Appl. No.: 09/018,990
[22] Filed: Feb. 5, 1998
[51] Int. Cl.[6] ....................................................... B08B 3/04
[52] U.S. Cl. ..................... 134/58 R; 134/57 R; 134/184; 134/188; 134/901
[58] Field of Search ................................. 134/58 R, 57 R, 134/901, 184, 188, 140, 135

[56] References Cited

U.S. PATENT DOCUMENTS

| | | | |
|---|---|---|---|
| 729,536 | 6/1903 | Brown . | |
| 2,744,635 | 5/1956 | Hiss . | |
| 3,085,583 | 4/1963 | Siek . | |
| 3,132,657 | 5/1964 | Ciccone . | |
| 3,376,878 | 4/1968 | Shoemaker | 134/183 |
| 4,700,729 | 10/1987 | Thaler | 134/139 |
| 4,710,233 | 12/1987 | Hohmann et al. | 134/1 |
| 4,721,124 | 1/1988 | Tuerkheimer et al. | 134/138 |
| 4,922,939 | 5/1990 | Adamczyk | 134/140 |
| 4,986,290 | 1/1991 | Oguma et al. | 134/95 |
| 4,995,409 | 2/1991 | Watts | 134/58 R |
| 5,117,849 | 6/1992 | Zimmerli | 134/57 R |
| 5,143,104 | 9/1992 | Iba et al. | 134/135 |
| 5,164,166 | 11/1992 | Stepanski et al. | 422/297 |
| 5,366,078 | 11/1994 | Braun | 206/5.1 |
| 5,421,353 | 6/1995 | Jakubowski | 134/58 R |
| 5,494,531 | 2/1996 | Azuma | 134/25.4 |
| 5,520,277 | 5/1996 | Alvord | 206/5.1 |
| 5,609,837 | 3/1997 | Cerny et al. | 422/301 |
| 5,690,211 | 11/1997 | Jao et al. | 206/5.1 |
| 5,758,675 | 6/1998 | Scheyer | 134/148 |

*Primary Examiner*—Frankie L. Stinson
*Assistant Examiner*—Paul J. Lee

[57] ABSTRACT

A denture cleaner is provided including a housing adapted to contain a cleaning fluid. Also included is an agitator assembly for forcing the cleaning fluid upwardly when actuated. Next provided is a lid mounted on the housing with clamps for connecting dentures thereto. The lid is removably mounted on the housing thereby cleaning the dentures when the agitator assembly is actuated.

7 Claims, 3 Drawing Sheets

DENTURE CLEANSER

BACKGROUND OF THE INVENTION

1. Field of the Invention

The present invention relates to denture cleaner systems and more particularly pertains to a new denture cleanser for cleaning dentures with agitated cleaning fluid.

2. Description of the Prior Art

The use of denture cleaners is known in the prior art. More specifically, denture cleaners heretofore devised and utilized are known to consist basically of familiar, expected and obvious structural configurations, notwithstanding the myriad of designs encompassed by the crowded prior art which have been developed for the fulfillment of countless objectives and requirements.

Known prior art denture cleaner systems include U.S. Pat. No. 4,922,939; U.S. Pat. No. 4,352,361; U.S. Pat. No. 4,157,922; U.S. Pat. Des. 261,423; U.S. Pat. No. 5,265,628; and U.S. Pat. No. 5,421,353.

In these respects, the denture cleanser according to the present invention substantially departs from the conventional concepts and designs of the prior art, and in so doing provides an apparatus primarily developed for the purpose of cleaning dentures with agitated cleaning fluid.

SUMMARY OF THE INVENTION

In view of the foregoing disadvantages inherent in the known types of denture cleaner systems now present in the prior art, the present invention provides a new denture cleanser construction wherein the same can be utilized for cleaning dentures with agitated cleaning fluid.

The general purpose of the present invention, which will be described subsequently in greater detail, is to provide a new denture cleanser apparatus and method which has many of the advantages of the denture cleaner systems mentioned heretofore and many novel features that result in a new denture cleanser which is not anticipated, rendered obvious, suggested, or even implied by any of the prior art denture cleaner systems, either alone or in any combination thereof.

To attain this, the present invention generally comprises a housing having a frusto-conical configuration. As best shown in FIG. 5, the housing defines a hollow interior and an open top with an upper peripheral edge. The housing includes a horizontally oriented divider integrally coupled at a central extent of the housing. The divider defines an upper compartment and a lower compartment. Coupled over the upper compartment adjacent to the open top of the housing is a meshed screen. An elastomeric annular bushing is mounted around the meshed screen just inward and below the upper peripheral edge. In operation, the upper compartment serves to contain a cleaning fluid. Next provided is an agitator assembly including a motor mounted within the lower compartment with a rotor. Such rotor is adapted to rotate upon the receipt of power. A turbine is rotatably coupled to the divider and fixedly coupled to the rotor of the motor for rotating coincidentally therewith which forces the cleaning fluid upwardly. For allowing the selective determination of a speed of the rotation of the rotor, a speed selector is connected between a power source and the motor. Such selector is further positioned on an exterior surface of the housing for being readily accessible. The agitator assembly lastly includes an actuator switch having a pair of contacts connected between the power source and the motor. The contacts are positioned on the upper peripheral edge for allowing the supply of power to the motor only upon being electrically connected. Finally, a transparent lid unit includes a circular top face and a periphery coupled to the top face. The periphery depends downwardly from the top face for defining an interior space and a lower peripheral edge. In use, the periphery is adapted to be removably rested on the bushing of the housing. The top face of the lid unit has a lower surface including a pair of resilient C-shaped clamps for releasably securing to a pair of dentures. The lid unit further includes an actuator assembly mounted to the periphery of the lid unit. A pair of contacts are mounted on the lid unit for communicating with those of the agitator assembly when the lid is rested on the housing. Connected to the contacts of the actuator assembly is a momentary switch for electrically connecting the contacts of the actuator assembly only when biased.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new denture cleanser apparatus and method which has many of the advantages of the denture cleaner systems mentioned heretofore and many novel features that result in a new denture cleanser which is not anticipated, rendered obvious, suggested, or even implied by any of the prior art denture cleaner systems, either alone or in any combination thereof.

It is another object of the present invention to provide a new denture cleanser which may be easily and efficiently manufactured and marketed.

It is a further object of the present invention to provide a new denture cleanser which is of a durable and reliable construction.

An even further object of the present invention is to provide a new denture cleanser which is susceptible of a low cost of manufacture with regard to both materials and labor, and which accordingly is then susceptible of low prices of sale to the consuming public, thereby making such denture cleanser economically available to the buying public.

Still yet another object of the present invention is to provide a new denture cleanser which provides in the apparatuses and methods of the prior art some of the advantages thereof, while simultaneously overcoming some of the disadvantages normally associated therewith.

Still another object of the present invention is to provide a new denture cleanser for cleaning dentures with agitated cleaning fluid.

Even still another object of the present invention is to provide a new denture cleanser that includes a housing adapted to contain a cleaning fluid. Also included is an agitator assembly for forcing the cleaning fluid upwardly when actuated. Next provided is a lid mounted on the housing with clamps for connecting dentures thereto. The lid is removably mounted on the housing thereby cleaning the dentures when the agitator assembly is actuated.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
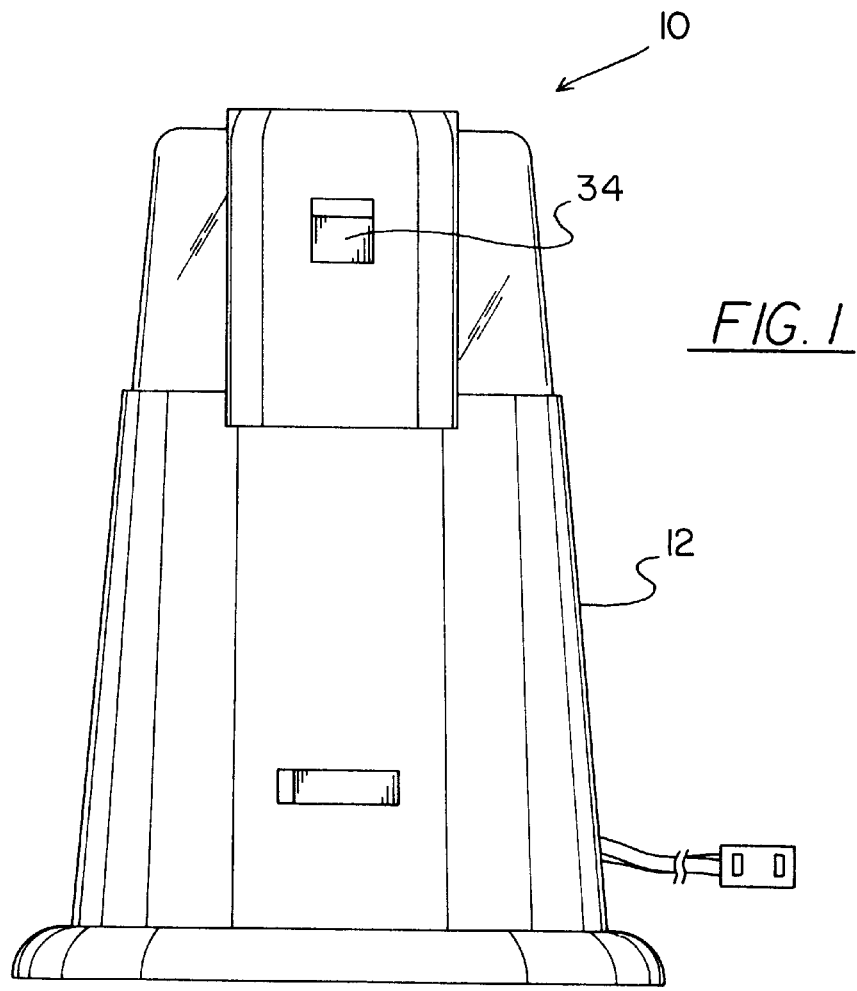
FIG. 1 is a side view of a new denture cleanser according to the present invention.
Figure 2:
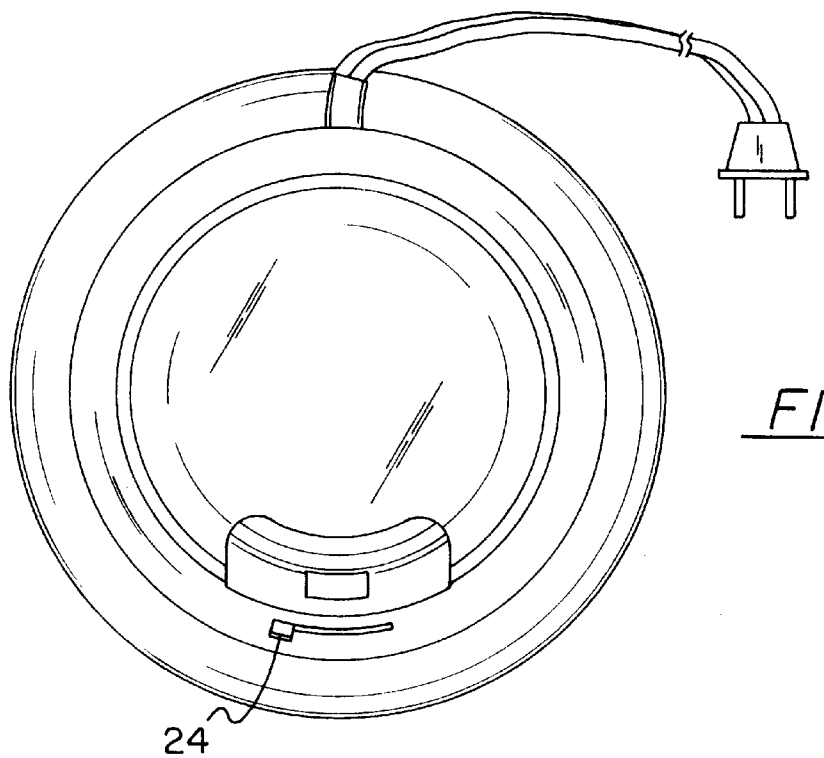
FIG. 2 is a top view of the present invention.
Figure 3:
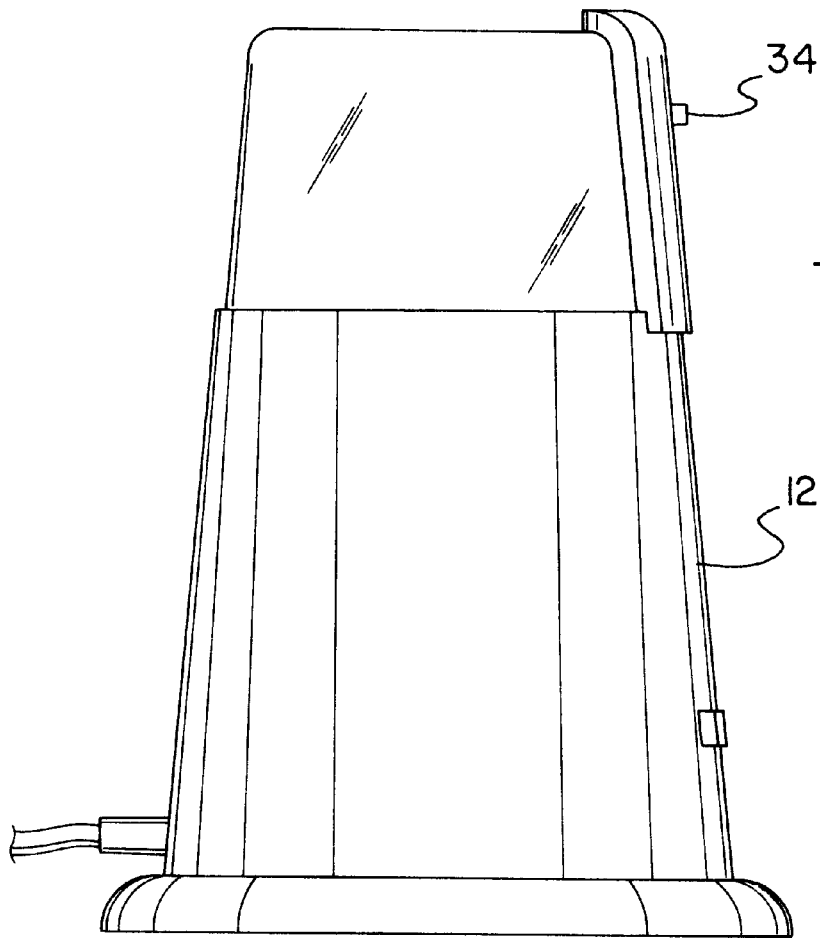
FIG. 3 is another side view of the present invention.
Figure 4:
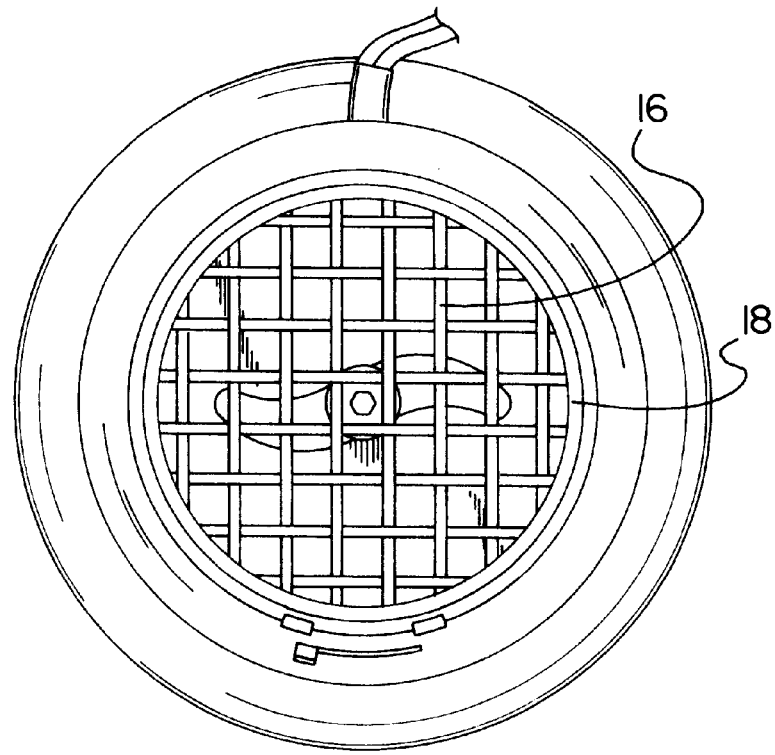
FIG. 4 is a top view of the present invention with the lid unit removed.

With reference now to the drawings, and in particular to FIGS. 1 through 6 thereof, a new denture cleanser embodying the principles and concepts of the present invention and generally designated by the reference numeral 10 will be described.

Figure 5:
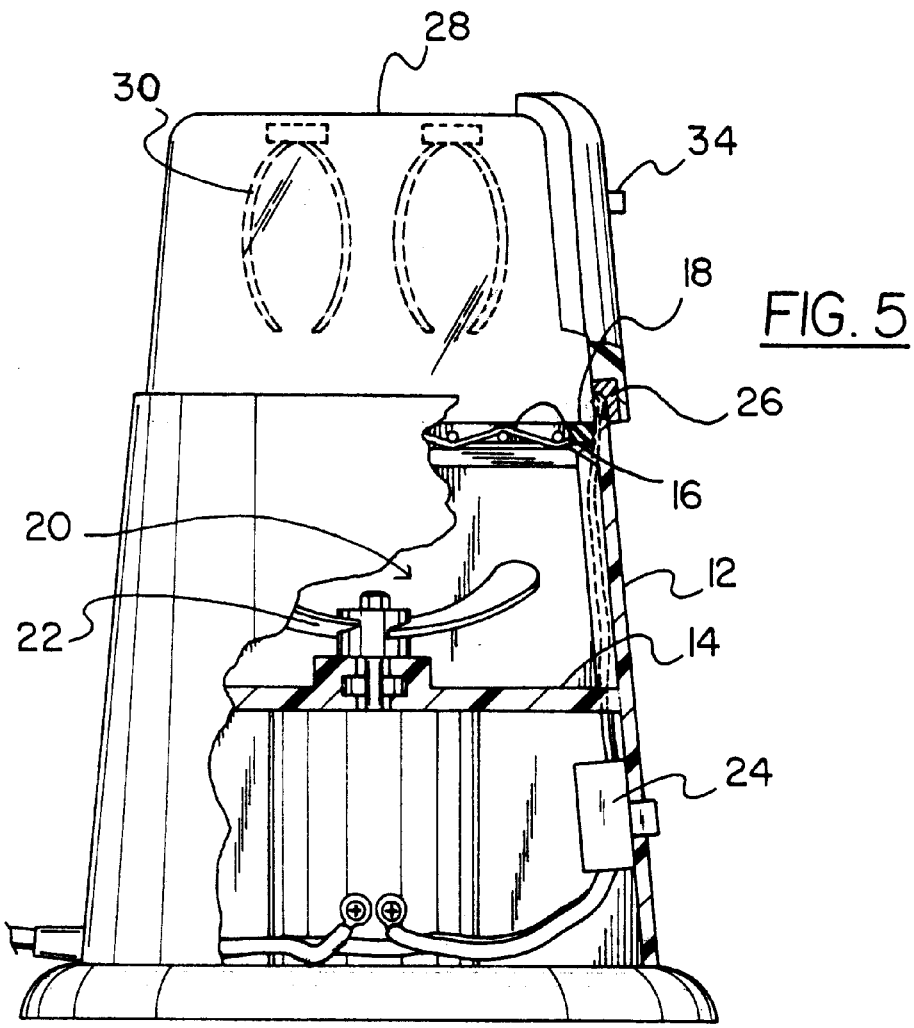
FIG. 5 is a side sectional view of the present invention.
Figure 6:
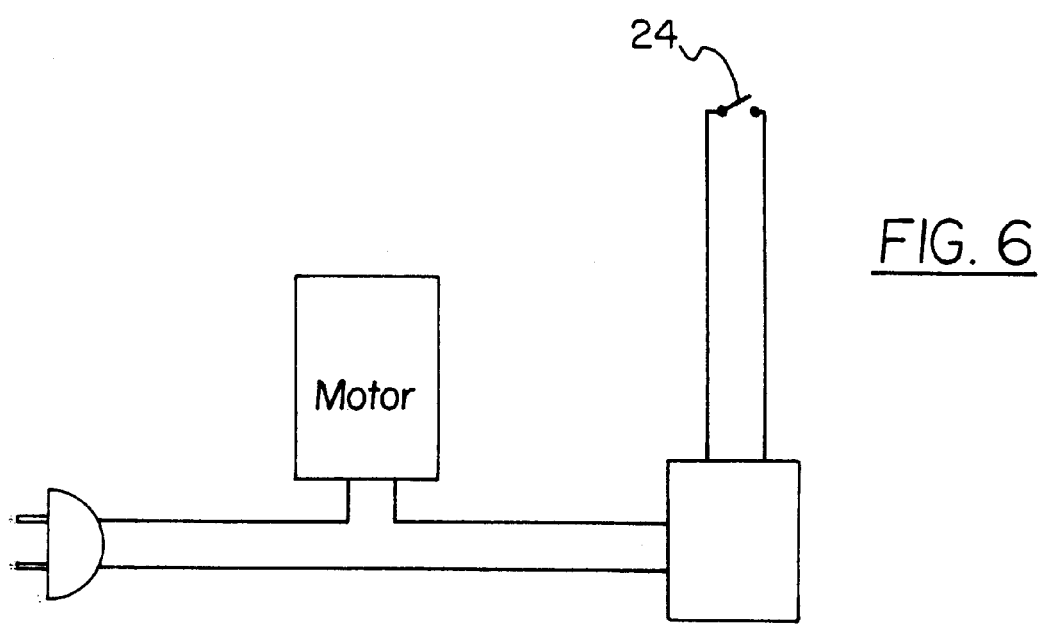
FIG. 6 is a schematic diagram of the various electrical components of the present invention.

The present invention, designated as numeral 10, includes a housing 12 having a frusto-conical configuration. As best shown in FIG. 5, the housing defines a hollow interior and an open top with an upper peripheral edge. The housing includes a horizontally oriented divider 14 integrally coupled at a central extent of the housing. The divider defines an equally sized upper compartment and lower compartment. Coupled over the upper compartment adjacent to the open top of the housing is a meshed screen 16. An elastomeric annular bushing 18 is mounted around the meshed screen just inward and below the upper peripheral edge. In operation, the upper compartment serves to contain a cleaning fluid.

Next provided is an agitator assembly 20 including a motor mounted within the lower compartment with a rotor. Such rotor is adapted to rotate upon the receipt of power. A turbine 22 is rotatab,ly coupled to the divider and fixedly coupled to the rotor of the motor for rotating coincidentally therewith which forces the cleaning fluid upwardly. The turbine has a length which approximately equal to a diameter of the housing.

For allowing the selective determination of a speed of the rotation of the rotor, a speed selector 24 is connected between a power source and the motor. It should be noted that the power source consists of an alternating current receptacle. Such selector is further positioned on an exterior surface of the housing for being readily accessible. The agitator assembly lastly includes an actuator switch 26 having a pair of spaced contacts connected between the power source and the motor. The contacts are positioned on the upper peripheral edge of the housing for allowing the supply of power to the motor only upon being electrically connected.

Finally, a transparent lid unit 28 includes a circular top face and a periphery coupled to the top face. The periphery depends downwardly from the top face for defining an interior space and a lower peripheral edge. In use, the periphery is adapted to be removably rested on the bushing of the housing. The top face of the lid unit has a lower surface including a pair of resilient C-shaped clamps 30 for releasably securing to a pair of dentures. The lid unit further includes an actuator assembly mounted to the periphery of the lid unit. As shown in FIG. 5, the clamps extend downwardly to a point adjacent the lower peripheral edge of the lid unit.

The actuator assembly includes a pair of contacts mounted on the lid unit for communicating with those of the agitator assembly when the lid is rested on the housing. Connected to the contacts of the actuator assembly is a momentary switch 34 for electrically connecting the contacts of the actuator assembly only when biased. As such, the contacts of the agitator assembly may be closed when the lid unit is in place. The momentary switch is a slider switch which has a biased closed orientation and an unbiased open orientation.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A denture cleaner comprising, in combination:

a housing having a frusto-conical configuration and defining a hollow interior and an open top with an upper peripheral edge, the housing including a horizontally oriented divider integrally coupled at a central extent of the housing thereby defining an upper compartment and a lower compartment, a meshed screen coupled over the upper compartment adjacent to the open top of the housing, and an elastomeric annular bushing mounted around the meshed screen just inward and below the upper peripheral edge, wherein the upper compartment is adapted to contain a cleaning fluid;

an agitator assembly including a motor mounted within the lower compartment with a rotor adapted to rotate upon the receipt of power, a turbine rotatably coupled to the divider and residing within the lower compartment with the turbine being coupled to the rotor of the motor for rotating coincidentally therewith which forces the cleaning fluid upwardly, a speed selector connected between a power source and the motor and further positioned on an exterior surface of the housing for allowing the selective determination of a speed of the rotation of the rotor of the motor, and an actuator switch including a pair of contacts connected between the power source and the motor and further positioned on the upper peripheral edge for allowing the supply of power to the motor only upon being electrically connected;

a transparent lid unit including a circular top face and a periphery coupled to the top face and depending downwardly therefrom for defining an interior space and a lower peripheral edge adapted to be removably rested on the bushing of the housing, the top face of the lid unit having a lower surface including a pair of resilient C-shaped clamps for releasably securing to a pair of dentures, the lid unit further including an actuator assembly mounted to the periphery of the lid unit and having a pair of contacts mounted thereon for communicating with those of the agitator assembly when the lid is rested on the housing and a momentary switch connected to the contacts of the actuator assembly for electrically connecting the contacts of the actuator assembly only when biased.

2. A denture cleaner comprising:

a housing adapted to contain a cleaning fluid with an upper peripheral edge having a bushing mounted thereon;

an agitator assembly situated within the housing for forcing the cleaning fluid upwardly when actuated;

a lid having a top face with a periphery depending downwardly therefrom for defining a lower peripheral edge which is removably rested on the bushing of the housing with a pair of resilient C-shaped clamps, for releasably securing a pair of dentures, depending from the top face of the lid and residing entirely above the lower peripheral edge of the lid for connecting dentures thereto, thereby cleaning the dentures when the agitator assembly is actuated;

wherein a screen is situated between the agitator assembly and the pair of resilient C-shaped clamps; and wherein the screen is mounted to the housing.

3. A denture cleaner as set forth in claim 2 wherein the agitator assembly is capable of being actuated only when the lid is rested on the housing by way of a switch mechanism mounted on the upper peripheral edge of the housing.

4. A denture cleaner as set forth in claim 2 wherein the lid is transparent.

5. A denture cleaner as set forth in claim 2 wherein the agitator assembly includes a turbine.

6. A denture cleaner as set forth in claim 2 wherein a screen is situated between the agitator assembly and the at least one clamp and is mounted to the housing.

7. A denture cleaner as set forth in claim 2 wherein the at least one clamp includes fingers which depend downwardly in a substantially vertical orientation.

* * * * *